United States Patent [19]
Green et al.

[11] Patent Number: 5,895,747
[45] Date of Patent: Apr. 20, 1999

[54] INHIBITION OF TAX-MEDIATED INCREASE IN DNA BINDING

[75] Inventors: Michael R. Green, Boylston; Susanne Wagner, Shrewsbury, both of Mass.

[73] Assignee: University of Massachusetts Medical Center, Worcester, Mass.

[21] Appl. No.: 08/518,849

[22] Filed: Aug. 24, 1995

Related U.S. Application Data

[63] Continuation of application No. 08/018,819, Feb. 18, 1993, abandoned.

[51] Int. Cl.$^6$ .................................................. G01N 33/53
[52] U.S. Cl. ........................ 435/7.1; 435/6; 435/7.93; 436/536; 436/518
[58] Field of Search .......................... 435/7.1, 6, 7.93; 436/536, 518

[56] References Cited

U.S. PATENT DOCUMENTS

| | | | |
|---|---|---|---|
| 5,412,087 | 5/1995 | McGall et al. | 536/24.3 |
| 5,439,829 | 8/1995 | Anderson et al. | 436/518 |
| 5,589,375 | 12/1996 | Ullrich et al. | 435/240.2 |
| 5,616,475 | 4/1997 | Wachsman et al. | 435/69.1 |
| 5,641,486 | 6/1997 | Hinrichs et al. | 424/139.1 |
| 5,693,759 | 12/1997 | Wachsman et al. | 530/350 |

OTHER PUBLICATIONS

Tan et al., (Biological Abstracts) "Utilization of signal transduction pathway by the human T–cell . . . " J. Virol. 63(9):3761–3768, 1989.

Hai et al., (Biological Abstracts) "Transcription factor ATF complementary DNA clones an extensive . . . " Genes Dev. 3(12b):2083–2090, 1989.

Zhao et al. (1992) Proc. Natl. Acad. Sci. USA. Human T–cell Lymphotrophic Virus Type I (HTLV–I) Transcriptional Activator, Tax, Enhances CREB Binding to HTLV–I 21–Base–Pair Repeats by Protein–Protein Interaction. vol. 89, pp. 7070–7074, 1992.

Mosch et al. (1991) J. Biol. Chem. Transcriptional Activation of Yeast Nucleotide Biosynthetic Gene ADE4 by GCN4, vol. 266, No. 30, pp. 20453–20456, 1991.

Matthews et al., "In Vitro Activation of Transcription by the Human T–Cell Leukemia Virus Type I Tax Protein" Molecular and Cellular Biology, 12:1986–1996, (1992).

Suzuki et al., "The Trans–activiator Tax of Human T–cell Leukemia Virus . . . 21–Base–pair Enhacner of HTLV–1", Proc. Natl. Acad. Sci., USA 90:610–614, (1993).

Wagner et al., "HTLV–1 Tax Protein Stimulation of DNA Binding of bZIP Proteins by Enhancing Dimerization", Science, 262:395–399, (1993).

Zhao et al., Human T–cell Lymphotropic Virus Type I (HTLV–1) . . . Repeats by Protein–protein Interaction, Proc. Natl. Acad. Sci. USA 89:7070–7074, (1992).

Zhao et al., "Interaction of the Human T–cell Lymphotropic Virus Type I (HTLV–I) . . . Specifically to the 21–base–pair repeats in the HTLV–I Enhacner", Proc. Natl. Acad. Sci. USA, 88:11445–11449, (1991).

Wagner, S. et al., (1993), Science, 262:395–399.

L.J. Zhao and C.Z. Giam, "Interaction of The Human T–Cell Lymphotrophic Virus Type I (HTLV–I) Transcriptional Activator Tax With Cellular Factors That Bind Specifically to The 21–Base–Pair Repeats un the HTLV–I Enhancer", Proc. Natl. Acad. Sci. USA 88: 11445–11449, (1991).

Suzuki et al., "The Trans–Activator Tax of Human T–Cell Leukemia Virus Type 1 (HTLV–1) Interacts with cAMP–Responsive Element (CRE) Binding and CRE Modulator Proteins that Bind to the 21–Base–Pair Enhancer of HTLV–1", Proc. Natl. Acad. Sci. USA 90: 610–614, (1993).

L.J. Zhao and C.Z. Giam, "Human T–Cell Lypmhotropic Virus Type I (HTLV–I) Transcriptional Activator, Tax, Enhances CREB Binding to HTLV–I 21–Base–Pair Repeats by Protein–Protein Interaction", Proc. Natl. Acad. Sci. USA 89: 7070–7074, (1992).

Primary Examiner—Robert A. Wax
Assistant Examiner—Enrique D. Longton
Attorney, Agent, or Firm—Fish & Richardson, P.C.

[57] ABSTRACT

The Tax protein of Human T Cell Leukemia Virus Type 1 (HTLV-I) transcriptionally activated the HTLV-I promoter through binding sites for ATF, a family of cellular bZIP transcription factors. In this disclosure, it is reported that Tax dramatically increases the in vitro DNA binding activity of multiple ATF proteins. Tax also stimulates DNA binding of related bZIP proteins but does not affect the activity of proteins lacking a bZIP domain. The increased DNA binding activity occurs by a novel mechanism in which Tax promotes homodimerization in the absence of DNA. The elevated concentration of the bZIP homodimer results in increased DNA binding.

7 Claims, No Drawings

INHIBITION OF TAX-MEDIATED INCREASE IN DNA BINDING

This is a continuation of application Ser. No. 08/018,819, filed Feb. 18, 1993, now abandoned.

BACKGROUND OF THE INVENTION

Human T-cell leukemia virus Type 1 (HTLV-I) is associated with malignant adult T-cell leukemia (ATL) and has recently been linked to two degenerative neurologic diseases, HTLV-I associated myelopathy and multiple sclerosis. Viral replication is dependent upon the viral Tax protein, which transcriptionally activates the HTLV-I LTR and can also activate cellular and other viral promoters. The ability of HTLV-I to induce malignant transformation of cultured cells also requires a functional Tax gene.

Transcriptional activation of the HTLV-I LTR by Tax involves three 21 bp repeats, referred to as Tax-response elements (TRE). Mutational analysis indicated that the critical region of each 21 bp repeat is an ATF binding site. ATF proteins (ATFs) are a family of cellular transcription factors that contain homologous basic region/leucine zipper DNA binding (bZIP) domains. Several ATFs have been shown to bind to TRE sequences. These and other observations suggest that Tax, which is not a sequence-specific DNA binding protein, functions through ATFs to stimulate transcription.

SUMMARY OF THE INVENTION

The subject invention relates to a method for inhibiting Tax-mediated increase in DNA binding of a bZIP-containing protein e.g., ATF and AP-1). Dimerization, and consequently DNA binding, is inhibited by interfering with the binding of Tax to the bZIP domain of the bZIP-containing protein. Examples of inhibitory molecules which fall within the scope of the invention are peptides, antibodies and small organic molecules (e.g., members of a small molecule library).

The inhibition of Tax-mediated increase in DNA binding can be exploited in a method for inhibiting HTLV-1 replication or HTLV-1 induced malignant transformation. An inhibitory molecule which interferes with the binding of Tax to a bZIP domain in a bZIP-containing protein is introduced into HTLV-1 infected cells. The introduction of the inhibitory molecule interferes with the binding of Tax to the bZIP domain thereby inhibiting dimerization of the bZIP-containing protein. This inhibition of dimerization prevents the increase in DNA binding affinity which accompanies dimerization.

DETAILED DESCRIPTION OF THE INVENTION

It had been previously reported that trans-activation by Tax was most likely mediated by interaction of Tax with activating factors which interact directly with DNA thereby stimulating transcription. However, the specific nature of the interaction between Tax and the activating factors had not been elucidated. The discovery of a direct interaction between Tax and the bZIP domain of such activating factors suggests a method for intervention in Tax-mediated control of gene expression by inhibiting the binding of Tax to the bZIP domain. Intervention in this manner prevents increased dimerization and the accompanied increase in DNA binding affinity.

Tax-mediated dimerization can be inhibited, for example, by contacting at least one of the members of the Tax::bZIP-containing protein binding pair (referred to herein as the "Tax::bZIP binding pair") with an inhibitory molecule which interferes with the binding of Tax to the bZIP domain. Experiments described in the Exemplification section below define a minimal bZIP peptide comprising amino acids 350–415 of the ATF2 protein with which the Tax protein interacts directly. The Exemplification also demonstrates that the bZIP-containing AP-1 family of transcription factors are Tax-responsive. Two particularly important members of the AP-1 family are the c-jun and c-fos proteins which are known oncoproteins. The activity of other known DNA binding proteins was unaffected by incubation with the Tax protein. Thus, stimulation of DNA binding activity by Tax is specific for proteins which contain the bZIP motif.

The inhibitory molecule can be, for example, a peptide. Since it has been demonstrated that the Tax protein interacts directly with the bZIP domain of ATF, a peptide mimic of the bZIP domain can be used to inhibit the dimer-promoting activity of Tax. A mimic peptide, when introduced into an incubation mixture containing Tax and a bZIP-containing moiety will compete for Tax binding with the bZIP-containing moiety. Mimic peptides which compete successfully will function to interfere with the promotion of dimerization in the incubation mixture.

In addition to peptides, small organic molecules can be tested for inhibitory activity with a high probability of success. Libraries of small organic molecules are frequently employed by pharmaceutical companies in an effort to identify agonistic or antagonistic agents. Natural product extracts or crude broth from the growth of cells in culture represent other source to be examined for the presence of inhibitor molecules.

Antibodies can also be used to interfere with the formation of the Tax::bZIP binding pair. Preferably, the an antibody to be used for this purpose is a monoclonal antibody. Conventional methods can be used to generate and screen monoclonal antibodies to be used for this purpose.

The identification of inhibitor molecules is facilitated by the use of a high throughput screening assay. Such an assay can be designed to efficiently screen large numbers of molecules. For example, a bZIP-containing moiety can be fixed to the wells of a multi-welled plate. Incubation mixtures are formed in the wells of the plate by adding an appropriately buffered solution, and detectable (e.g., fluorescently labeled) Tax protein. Potential inhibitor molecules are screened by adding such molecules, in appropriate concentrations to individual incubation mixtures and monitoring the effect of the added molecules on the binding of Tax to the bZIP-containing moiety.

If the molecule being tested for the ability to interfere with the formation of the Tax::bZIP binding pair does, in fact, possess the desired property, the observed result will be a decrease in the level of binding of the labeled Tax protein to the bound bZIP-containing moiety in the incubation mixture. Molecules which do not bind to a member of the Tax::bZIP binding pair would be predicted to have no effect on the binding of Tax to the fixed bZIP moiety in the binding assay described.

It should be recognized that an inhibitory molecule identified by this type of screening method can function by binding to either member of the Tax::bZIP binding pair. Although an inhibitory molecule which binds to either member of the Tax::bZIP binding pair would function to inhibit dimerization and DNA binding, the inhibitory molecule preferably binds to the Tax protein. Tax binding is preferable since the bZIP-containing protein, which is likely to play a role in desirable cellular functions, would not be directly affected.

Inhibitory molecules identified in this manner can be used in a variety of ways. For example, since it has been demonstrated herein that the trans-activating activity of Tax is a consequence of the Tax-mediated dimerization of bZIP-containing proteins, it can be predicted that interference with dimerization will depress the trans-activating capabilities of Tax. Thus, an inhibitory molecule identified by the methods described above, or a derivative of such a molecule, can be exploited in a method for inhibiting HTLV-1 replication by or HTLV-1 induced malignant transformation introducing the inhibitory molecule into HTLV-1 infected cells. Methods for the introduction of such molecules into infected cells are well known in the art.

EXEMPLIFICATION

Tax Increases the DNA Binding Activity of Multiple ATFs

To investigate the possible effect of Tax on ATF DNA binding activity, three ATFs (ATF-1, ATF-2 and CREB) were initially purified as glutathione-S-transferase (GST)-fusion proteins and assayed for binding to a DNA oligonucleotide containing the most distal TRE element of the HTLV-I LTR. DNA binding reactions were performed using protein concentrations that gave rise to a low level of DNA binding in the absence of Tax. More specifically, binding reactions contained approximately 50 ng of affinity-purified fusion protein and approximately 200 ng purified Tax protein. Under the conditions of the DNA binding assay, addition of purified Tax greatly increased DNA binding. DNA binding was not increased upon addition of an irrelevant protein or following heat treatment of Tax. As expected, there was no detectable interaction between purified Tax and DNA. DNA binding of ATF derivatives lacking the GST moiety, such as histidine-ATF2 and a minimal bZIP peptide was comparably enhanced by Tax, excluding the possibility that the GST moiety was involved in the Tax-mediated DNA binding increase.

Tax Functions through a Minimal bZIP Domain

To define the portion of ATF required for Tax-responsiveness, several GST-ATF2 deletions were analyzed. A GST-ATF2 fusion containing the minimal bZIP domain (amino acids 350 to 415) supported the Tax-mediated increased in DNA binding. This result is consistent with the fact that Tax increased DNA binding of multiple ATFs, and the bZIP is the only region of significant homology among ATF proteins.

Tax Interacts with the bZIP-DNA Complex

A striking observation was that while Tax increased DNA binding in the DNA binding assay, the electrophoretic mobility of the ATF-DNA complex was the same in the presence or absence of Tax. One plausible explanation for this result was that Tax dissociated from the ATF-DNA complex during electrophoresis in the non-denaturing gel. To address this possibility DNA binding was analyzed in several other non-denaturing gel systems. In a Tris-glycine buffer the addition of Tax gave rise to a second DNA-protein complex of reduced electrophoretic mobility. This "super-shifted" complex was eliminated following heat-inactivation of Tax. Similar results were obtained with GST-ATF1 and GST-ATF2.

To confirm that Tax was indeed a component of the ATF-DNA complex a coimmunoprecipitation experiment was performed. DNA binding reactions were prepared which contained a $^{32}$P-labeled DNA probe, and a minimal ATF-2 bZIP domain, in the presence and absence of Tax. Following incubation, an α-Tax antibody was added to immunoprecipitate the $^{32}$P-labeled DNA probe. The results show that the α-Tax antibody could immunoprecipitate the $^{32}$P-labeled DNA probe, but only if both Tax and the ATF-2 bZIP were present. Immunoprecipitation of the $^{32}$P-labeled DNA probe was not observed using a control serum. These combined results clearly indicate that there is a ternary complex containing the DNA-bound bZIP protein and Tax. DNAse I protection and ultraviolet light crosslinking experiments failed to reveal an interaction between Tax and DNA. These results, combined with the data discussed above and below, indicate that in the ternary complex Tax directly interacts primarily (or exclusively) with the minimal bZIP domain.

Tax-Mediated Enhancement of DNA Binding is Specific for bZIP Proteins

To assess the specificity of Tax-mediated enhancement of DNA binding, the electrophoretic mobility-shift assay was used to test several other well-characterized transcription factors. The AP-1 family of transcription factors are closely related to ATF proteins (reviewed by Angel and Karin, *Biochimica et Biophysica Acta* 1072: 129 (1991)). AP-1 proteins also contain bZIP domains and bind a DNA sequence (5'-TGACTCA-3'), which differs in only one position from an ATF consensus site (5'-TGACGTCA-3'). The yeast transcription factor GCN4 is a prototype AP-1 protein. The DNA binding activity of a peptide comprising the GCN4 bZIP domain was responsive to Tax in a manner similar to bacterially expressed ATFs. In contrast, neither the DNA binding of a GST-myogenin fusion protein, a helix-loop-helix protein, nor binding of GAL4-AH, a zinc-finger type protein, was significantly increased by Tax. Thus, stimulation of DNA binding activity by Tax appears to be specific for proteins containing a bZIP motif.

The Tax-Mediated DNA Binding Increase is Dependent on the Concentration of the bZIP To investigate the role of bZIP concentration the effect of Tax was measured at GCN4 concentrations ranging from 0.04 nM to 40 nM. More specifically, GCN4 peptide, at varying concentrations, was assayed for DNA binding to a collagen TRE oligonucleotide in the absence and presence of Tax. DNA binding reactions were evaluated using a PhosphorImager (Molecular Dynamics) and Imagequant™ software. Maximal stimulation of DNA binding was observed at peptide concentrations below 4 nM and at higher protein concentrations Tax did not significantly increase DNA binding. The failure to increase DNA binding at high GCN4 concentration is not due to limiting Tax: increasing Tax concentration did not affect DNA binding at higher peptide concentrations. These results suggest that Tax overcomes a concentration-dependent step that normally limits the extent of DNA binding.

Tax Increases Formation of bZIP Homodimers in the Absence of DNA bZIP proteins bind DNA as dimers and dimerization occurs prior to and is a prerequisite for DNA binding. Tax could therefore stimulate DNA binding by increasing either dimerization of the bZIP or the subsequent interaction between the bZIP homodimer and DNA. The effect of Tax on dimerization of the bZIP domain was measured using a well described chemical cross-linking assay. Previous studies have shown that the subunits of bZIP dimers can be crosslinked to one an other with glutaraldehyde, a bifunctional crosslinking reagent. GST-ATF2 (100–200 ng) was incubated in the presence or absence of Tax (200 ng), and following addition of glutaraldehyde (0.02% final concentration), the products were fractionated on a SDS-polyacrylamide gel and analyzed by immunoblotting with GST specific polyclonal antiserum. At low protein concentration, GST-ATF2 is predominantly a monomer and at an elevated GST-ATF2 concentration, homodimer formation increased, as expected. Significantly, addition of Tax dramatically increased the amount of-ATF-2 homodimers. At higher concentrations of glutaraldehyde additional crosslinked products were detected, which included Tax.

Tax Increases the Association Rate of DNA Binding

To investigate how Tax affects the kinetics of DNA binding, the association and dissociation rates of the bZIP-DNA complex in the presence and absence of Tax was measured. Binding reactions containing 50 ng purified GST-ATF2 protein were incubated in the presence or absence of 200 ng Tax protein and analyzed on a 0.5×TBE/5% polyacrylamide gel. In the absence of Tax, binding of GST-ATF2 to DNA reached a maximal level by 15 minutes. In the presence of Tax, total DNA binding was increased, as expected, and equilibrium was achieved after only 1 minute. Similar results were observed using the GCN4 peptide. These results indicate that Tax increases the on-rate of DNA binding.

To measure the dissociation rate of the bZIP-DNA complex, a reaction mixture was allowed to reach equilibrium, a 50-fold excess of specific competitor DNA (unlabeled LTR oligonucleotide) was added, and the amount of remaining bZIP-DNA complex was measured as a function of time. The data generated in this experiment indicates that bound ATF-2 dissociated from DNA at a comparable rate in the presence and absence of Tax. These results indicate that Tax increases the on-rate of the bZIP-DNA complex without significantly affecting the off-rate, thus, accounting for the observed DNA binding increase.

Other Observations

Regulating transcription factors at the level of DNA binding is one important means for controlling gene expression and several distinct mechanisms have been described. For example, the in vitro DNA binding activity of some AP-1 proteins can be regulated by redox (reduction-oxidation) involving a conserved cysteine residue within the basic region of the bZIP. Accordingly, reducing agents, such as DTT, greatly enhance DNA binding of *E. coli*-derived jun and fos proteins. However, Tax-mediated stimulation of DNA binding is indistinguishable in the absence or presence of DTT. Furthermore, the GCN4 peptide used in the above-described experiments lacks a cysteine residue, ruling out redox regulation. The DNA binding activity of some proteins can be stimulated by protein phosphorylation. However, Tax increased DNA binding in the absence of $Mg^{2+}$ and ATP indicating that phosphorylation was not involved.

The influence of auxiliary factors in modulating DNA binding has emerged from studies of several mammalian transcription factors. For example, dimerization of the homeodomain protein HNF-1α is stimulated by the co-factor DCoH. However, this affects the transcriptional activity of HNF-1α, not its DNA binding activity.

The effect of Tax on ATF binding is in some respects reminiscent of the induction of DNA binding observed for SRF and Phox1. However, one important difference concerns the effects of Tax on association and dissociation rates. It has been reported that Phox1 increases both the association- and the dissociation-rate of the SRF/SRE complex, and it has been proposed that an increased exchange of SRF on its binding site could allow for a faster response to transient mitogenic signals. Tax increases the association rate of the bZIP with DNA, without affecting the dissociation rate of the bZIP-DNA complex. The sum of these effects accounts for the enhanced DNA binding.

Equivalents

Those skilled in the art will recognize or be able to ascertain, using no more than routine experimentation, many equivalents to the specific embodiments of the invention described herein. Such equivalents are intended to be encompassed by the claims.

We claim:

1. A method for identifying molecules that reduce the Tax-mediated increase in DNA binding of a protein comprising a bZIP domain, said method comprising the following steps:

(a) fixing a peptide or protein comprising a bZIP domain to a solid support;

(b) contacting said peptide or protein comprising a bZIP domain with Tax protein in the presence and absence of a selected molecule;

(c) removing the fraction of said Tax protein that has not bound to said peptide or protein comprising a bZIP domain;

(d) measuring the fraction of said Tax protein bound to said peptide or protein comprising a bZIP domain; and (e) comparing the amount of Tax protein bound to said peptide or protein comprising a bZIP domain in the absence and presence of said selected molecule, whereby a reduction in the amount of Tax protein bound to said protein or peptide comprising a bZIP domain caused by said selected molecule indicates that said selected molecule reduces the Tax-mediated increase in DNA binding of bZIP-containing proteins.

2. The method of claim 1, wherein said selected molecule is an organic molecule.

3. The method of claim 1, wherein said peptide comprising a bZIP domain is a polypeptide fragment of a protein selected from the group consisting of ATF and AP-1 proteins.

4. The method of claim 3, wherein said AP-1 protein is selected from the group consisting of c-fos and c-jun.

5. The method of claim 1, wherein said selected molecule is an antibody.

6. The method of claim 1, wherein said selected molecule is a peptide.

7. The method of claim 1, wherein said peptide or protein comprising a bZIP domain is a polypeptide fragment of a protein.

* * * * *